(12) United States Patent
Lowe et al.

(10) Patent No.: US 8,736,281 B2
(45) Date of Patent: May 27, 2014

(54) SENSING SYSTEM AND METHOD

(76) Inventors: Christopher R. Lowe, Cambridge (GB);
Quentin Tannock, Cambridge (GB);
Adrian Stevenson, Cambridge (GB);
Karishma Jain, Cambridge (GB)

( * ) Notice: Subject to any disclaimer, the term of this patent is extended or adjusted under 35 U.S.C. 154(b) by 346 days.

(21) Appl. No.: 12/742,380

(22) PCT Filed: Nov. 28, 2008

(86) PCT No.: PCT/GB2008/003968
§ 371 (c)(1),
(2), (4) Date: Sep. 30, 2010

(87) PCT Pub. No.: WO2009/068886
PCT Pub. Date: Jun. 4, 2009

(65) Prior Publication Data
US 2012/0007607 A1    Jan. 12, 2012

(30) Foreign Application Priority Data
Nov. 30, 2007  (EP) .................................... 07121969

(51) Int. Cl.
*G01R 27/32* (2006.01)
*G01R 27/28* (2006.01)
*G01V 3/10* (2006.01)
*H04Q 5/22* (2006.01)
*H01C 7/00* (2006.01)
*G01H 1/00* (2006.01)

(52) U.S. Cl.
USPC ........ 324/639; 324/650; 324/326; 340/10.41; 338/34; 73/579

(58) Field of Classification Search
USPC ....................................................... 324/639
See application file for complete search history.

(56) References Cited

U.S. PATENT DOCUMENTS 4,224,595 A * 9/1980 Dolan ............................ 338/34
4,944,185 A * 7/1990 Clark et al. ..................... 73/579

(Continued)

FOREIGN PATENT DOCUMENTS

| DE | 102005043397 | 1/2007 | |
|---|---|---|---|
| WO | WO2004/053464 | 6/2004 | |
| WO | WO 2004053464 A1 * | 6/2004 | ............... G01N 3/62 |

OTHER PUBLICATIONS

Charles Hautamaki, Shayne Zurn, Susan C. Mantell, and Dennis L. Polla, Experimental Evaluation of MEMS Strain Sensors Embedded in Composites, Journal of Microelectromechanical Systems, vol. 8, No. 3, Sep. 1999.*

(Continued)

*Primary Examiner* — Patrick Assouad
*Assistant Examiner* — Christopher McAndrew
(74) *Attorney, Agent, or Firm* — Welsh Flaxman & Gitler LLC

(57) ABSTRACT

A sensing system comprises a material having a matrix structure in which a plurality of sensing elements are embedded, the sensing elements having electron distribution and/or transport properties that change in response to a change in a physical or chemical property of the material. The sensing system further comprises a receiver, including an antenna, the receiver arranged to receive a source RF signal and a returned RF signal, the returned RF signal being received from the material. A change in the electron distribution and/or transport properties of the sensing elements cause the source RF signal to change, such that a change in a property of the material can be determined from the returned RF signal. A corresponding method of sensing a change in a property of a material is also provided.

29 Claims, 8 Drawing Sheets

(56) References Cited

U.S. PATENT DOCUMENTS

| | | | | |
|---|---|---|---|---|
| 5,200,704 | A | * | 4/1993 | Clark et al. ............... 324/326 |
| 5,396,203 | A | * | 3/1995 | Hant ............... 333/248 |
| 5,827,980 | A | * | 10/1998 | Doemens et al. ........ 73/862.626 |
| 6,004,817 | A | * | 12/1999 | Chamberlain et al. ........ 436/56 |
| 6,037,180 | A | * | 3/2000 | Yorkgitis et al. ............... 436/56 |
| 6,480,141 | B1 | * | 11/2002 | Toth et al. ............... 342/22 |
| 6,532,824 | B1 | * | 3/2003 | Ueno et al. ............... 73/780 |
| 6,767,745 | B2 | * | 7/2004 | Chamberlain et al. ........ 436/56 |
| 6,801,131 | B2 | * | 10/2004 | Donskoy et al. ........... 340/573.1 |
| 7,088,111 | B2 | * | 8/2006 | Noujeim ............... 324/650 |
| 7,262,607 | B2 | * | 8/2007 | Champion et al. ........... 324/639 |
| 2006/0170535 | A1 | * | 8/2006 | Watters et al. ............ 340/10.41 |
| 2006/0253942 | A1 | * | 11/2006 | Barrera et al. ............... 977/852 |
| 2006/0290496 | A1 | * | 12/2006 | Peeters ............... 340/572.1 |
| 2007/0273390 | A1 | * | 11/2007 | Champion et al. ........... 324/639 |
| 2008/0087099 | A1 | * | 4/2008 | Allenberg et al. ........ 73/861.08 |
| 2008/0218416 | A1 | * | 9/2008 | Handy et al. ........... 343/700 MS |

OTHER PUBLICATIONS

Victor Giurgiutiu, Zao Chen, Frederic Lalande, Craig A. Rogers, Robert Quattrone and Justin Bennan, Passive and Active Tagging of Reinforced Composites for in Process and Infield Non-Destructive Evaluation, Feb. 26-29, 1996, 1996 SPIE Symposium on Smart Structures and Materials, Smart structures and Integrated Systems Conference.*

S. Zhou, C. Liang, C. A. Rogers, F. Sun and L. Vick, An in-situ sensory technique for in-service quality monitoring measurement of the complex Young's modulus of polymers, 14 ISPIE vol. 1918 Smart Sensing, Processing, and Instrumentation (1993), pp. 14-23.*

Suwei Zhou, Zaffir Chaudhry, and Craig A. Rogers, Robert Quatirone, Review of Embedded Particle Tagging Methods for NDE of Composite Materials and Structures, Apr. 20, 1995, SPIE vol. 2444 / pp. 39-52.*

F. P. Sun C. Liang C. A. Rogers and L. Vick, Magnetic activation of embedded sensory particles in active tagging interrogation of adhesive bonding, SPIE vol. 1918 Smart Sensing, Processing, and Instrumentation (1993), pp. 400-409.*

J. Chuang, D. J. Thomson, G. Bridges, Wireless strain sensor based on resonant RF cavities, Smart Structures and Materials 2004: Smart Structures and Integrated Systems, edited by Alison B. Flatau, Proc. of SPIE vol. 5390 (SPIE, Bellingham, WA, 2004), pp. 574-584.*

Dan G. Reed ,, Editor, The ARRL Handbook for radio communications 5005, the comprehensive RF Engineering Reference, Copyright 2005, ARRL—the national association for Amateur Radio Newington, CT 06111 USA, Eighty-Second Edition, pp. 16.1-16.4.*

Butler, JC et al., "Wireless, passive, resonant-circuit . . . sensor", Sensors and Actuators A, Elsevier Sequoia S.A., Lausanne, CH, vol. 102, No. 1-2, Dec. 1, 2002, pp. 61-66.

Chuang et al., "Wireless strain sensor", Proc. of SPIE Smart Structures and Materials 2004, vol. 5390, 2004, pp. 574-584.

Krantz et al., "Project update: applied research on remotely-queried embedded microsensors", SPIE Conference on Smart Electronics and MEMS, vol. 3673, 1999, pp. 157-164.

Yi, Jia et al., Design and characterization of a passive . . . sensor, Measurement of Science and Technology . . . , Bristol, GB, vol. 17, No. 11, Nov. 1, 2006, pp. 2869-2876.

* cited by examiner

SENSING SYSTEM AND METHOD

CROSS REFERENCE TO RELATED APPLICATIONS

The present application is the National Stage of International Application No. PCT/GB2008/003968, filed Nov. 28, 2008, entitled "SENSING SYSTEM AND METHOD", which claims the benefit of European Patent Application No. 07121969.5, filed Nov. 30, 2007, entitled "SENSING SYSTEM AND METHOD".

The present invention relates to a sensing system and method.

Structural health monitoring (SHM) is a field of technology that is attracting increasing interest in industries such as civil, structural and aerospace engineering. The aim of SHM is to collect data concerning critical structural elements using sensors, in order to provide indicators of anomalies detected in a structure, thereby monitoring its reliability and safety. Current SHM systems require the installation of one or more sensors at key points of any structure of interest, the type of sensor depending on specific parameters of interest to be sensed. This can make such systems expensive and time consuming to install, while real time, continuous monitoring of the sensors is in practice unrealistic.

One disadvantage of known systems is that the composite materials used in modern aircraft render current SHM technology obsolete, creating a demand within this industry that the current technology cannot meet.

Other industries in which composite materials are increasingly used are the oil and gas industry, in which monitoring of the fatigue of components such as seals and gaskets is critical, underground structures such as tunnels and pipeline networks, and military aircraft and submarine technology, where reliability and safety are paramount.

These advantages are relevant to the medical sector where implanted components, heart valves and hip joints need to be monitored for reliability and safety; for environmental sensing where contamination in water or air can be tracked with robust materials at low cost; for Advanced Manufacturing where materials, especially composite materials, can be tracked during the production process, to raise the quality of plastic parts; and for applications in hostile or inaccessible locations such as space or those using rotary components such as turbines.

The areas of technology described above require reliable and accurate wireless sensing in order to selectively or continuously monitor structures that are not immediately accessible for close inspection.

The present invention seeks to overcome the problems outlined above. According to the present invention there is provided a sensing system which comprises:

a material having a matrix structure in which a plurality of sensing elements are embedded, the sensing elements having electron distribution and/or transport properties that change in response to a change in a physical or chemical property of the material; and a receiver, including an antenna, the receiver arranged to receive a source RF signal and a returned RF signal, the returned RF signal being received from the material;

wherein a change in the electron distribution and/or transport properties of the sensing elements cause the source RF signal to change, such that a change in a property of the material can be determined from the returned RF signal.

The present invention also provides a method of sensing a change in a property of a material, the material having a matrix structure in which a plurality of sensing elements are embedded, the sensing elements having electron distribution and/or transport properties that change in response to a change in a physical or chemical property of the material, the method comprises the steps of:

interrogating the material with a source RF signal;
receiving a returned RF signal from the material; and
determining the change in the property of the material from a change in the returned RF signal that is caused by the change in the electron distribution and/or transport properties of the sensing elements. The invention will now be described in detail with reference to the accompanying drawings, in which.

Figure 1:
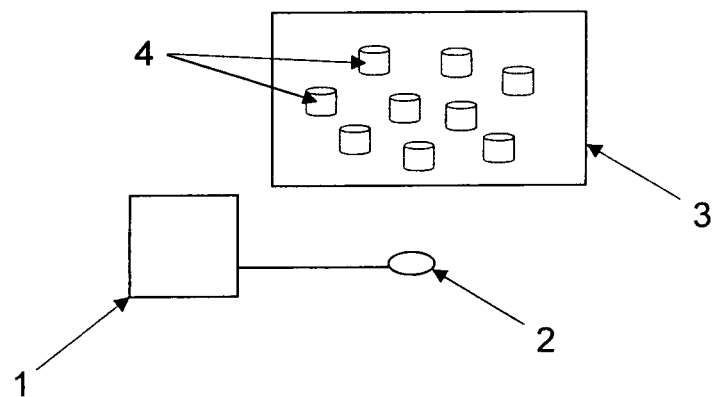
FIG. 1 is a schematic diagram of an example of a system according to the invention.

Referring to FIG. 1, a schematic diagram of a wireless transceiver 1 having an antenna 2 is shown. A portion of material 3, for example a polymer material, has a matrix structure in which multiple sensing elements 4 are embedded such that the sensing elements 4 are dispersed within and surrounded by the matrix material 3. The sensing elements 4 have electron distribution and/or transport properties that change in response to a change in a physical or chemical property of the material. This behaviour results in an alteration in a radio frequency (RF) signal (for example, a microwave signal) that is transmitted from the transceiver 1, via the antenna 2, to interrogate the matrix material 3, such that the change in the material can be determined from the received signal. In this way, the sensing elements 4 allow non-invasive, intrinsic sensing of a change in the properties of the material.

The radio transceiver 1 is constructed to generate a modulated radio frequency signal, which is either pulse, frequency, phase, or digitally modulated to reduce background noise, and to detect a returned signal from a structure formed of the matrix material 3 in real time. The returned radio signal is typically collected via a scatter, reflection, or transmission set-up. The transceiver 1 is designed to track key spectral features in the GHz region of the electromagnetic spectrum that are linked to the environment of the sensing elements. The net result is a change in the returned GHz spectra and the remote collection of information about the physical and chemical properties of the bulk material 3.

Figure 2:
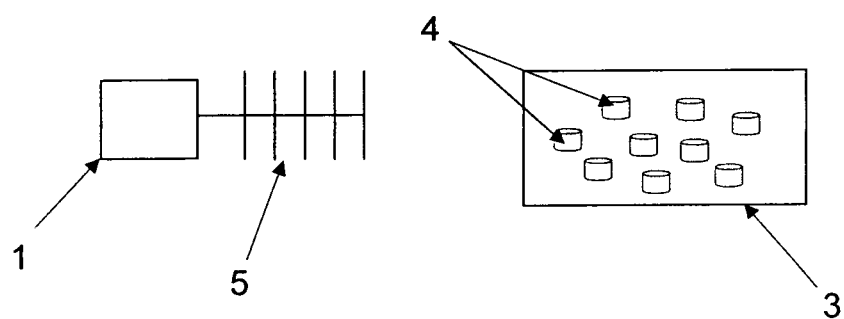
FIG. 2 is a schematic diagram of a further example of a system according to the invention.

The antenna 2 is arranged to radiate the radio frequency signal, and to collect the reflected signal at a high signal/noise ratio in real time. In use the antenna 2 applies the RF signal to the target site, which can be spread over a wide or narrow region of the material 3. This is particularly advantageous in structural components of, for example, aircraft, where the sensing can be focussed on either a specific, small area such as a seal or join or alternatively a large structure such as an entire wing. The antenna can be arranged to function like a radar based system, producing a narrow beam of GHz radiation according to wavelength. This behaviour is preferably achieved with parabolic or phase array antenna structures. FIG. 2 shows a further example of a sensing system, where the antenna is a directional antenna 5.

Another way of measuring bulk materials is based on the use of differential radio measurements. This embodiment of the invention would necessitate a total of signal sources and receivers greater than two. The advantage of this embodiment is that specific locations within a relatively large sample, such as a sheet or panel, can be resolved. The information allows an image of the bulk material properties to be formed, so that important physical/chemical information from a specific location can be obtained by combining the received signals.

In a preferred embodiment, the material in which the sensing elements 4 are supported is a polymer matrix such as an elastomer or epoxy matrix, and the addition of the sensing elements 4 therefore leads to the formation of a composite polymer matrix material 3. This material 3 is ideally insulating in order to allow it to support the efficient transmission of electromagnetic signals in the GHz range. The embedded elements 4 are used for sensing purposes, and further elements can be added to form additional sensing functions if required.

According to systems and methods of the current state of the art, a radio signal directed at a material is unable to extract information about the mechanical, electrical and chemical status of the material. However, adding sensing elements whose electron distribution and/or transport properties are altered by their local environment can make this monitoring function possible. The sensing elements 4 are arranged to alter properties such as the dielectric or magnetic properties of the material 3.

The sensing elements 4 comprise any particles that exhibit either a high quality resonance behaviour or a non-linear property that leads to harmonic generation and frequency doubling. Particles that can be used for this purpose include single wall carbon nanotubes, multiwall carbon nanotubes, nanorings of gold, magnetic particles, and many others. The underlying mechanism leading to the unusual radio properties can be acoustic, dielectric, piezoelectric, electrostrictive, magnetostrictive, conductive or semiconductive in origin. As a result properties such as the dielectric or magnetic properties of the materials change, which in turn alters the returned radio wave in specific ways. The type of particle is selected such that it responds to specific environmental changes such as strain, temperature, hydration or pH. To increase signal levels in more challenging environments, sensing particles can also be adsorbed to a second particle of low loss dielectric material which increases the electromagnetic resonance.

The sensing elements 4 may comprise particles, the resonance Q factor of which is changed by a change in an electrical and/or mechanical property of the material 3. For example, a mechanical change in the material 3 can lead to an increase in electrical resistance, which increases dielectric loss and lowers the Q factor of the material 3.

In order to gain these properties and deploy them usefully, a mechanism that links the radio waves to the particle is required. To achieve this, one of two mechanisms, or both mechanisms together, lead to the exchange of radio energy between the composite matrix material 3 and the transceiver and antenna device 1, 2, is employed.

A first coupling mechanism uses the presence of magnetic or electric dipoles within coherent dimensions, as defined by the size of the particles, as well as uniform dispersion of the particles through the polymer. The matrix particles are connected to the sensing particles via, for example, magnetostriction, converse piezoelectricity, magnetic direct generation or via traditional electron coupling that might occur between two wires. The coupling alone is not sufficient to establish a working sensor material; however, one difference in the behaviour of the sensing composite material, relative to other dielectric composite materials, is that a high-quality resonance appears in the radio signal reflected from this material. Therefore, in using the matrix material as a sensor, properties such as the electrical and/or mechanical properties of the material alter the resonance frequency of the particles uniformly in target locations, so the embedded particles change frequency by a similar increment, so the net signal is coherent.

Figure 3A:
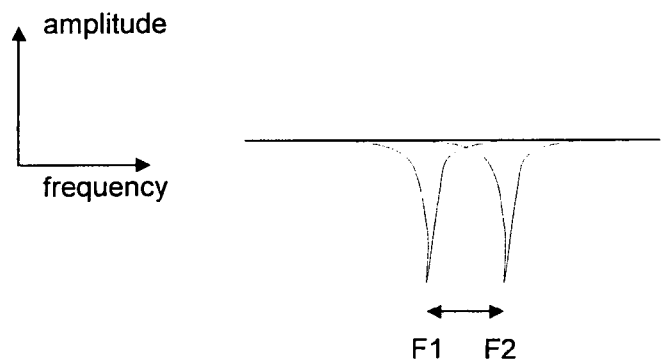
FIGS. 3a to 3c show examples of outputs obtained when employing a system according to the invention.
Figure 3B:
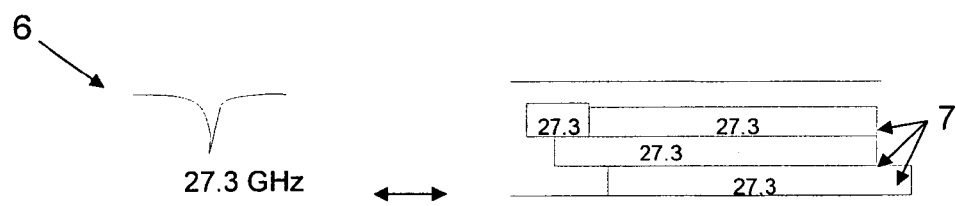

One way to monitor this first mechanism is by a passive resonant sensing method, as shown in FIGS. 3a and 3b. The resonance frequency of the matrix material 3, which is for example a polymer, is tracked as a function of time. FIG. 3a shows a typical system result that allows tracking of the returned RF signal frequencies. In this method, a change in the frequency spectrum of the returned signal indicates a change in the resonance frequency of the material.

Preferably, the sensing system further comprises circuitry arranged to determine at least one of the mechanical, electrical and chemical status of the material. An accurate and reliable way of determining the position and extent of any anomaly or fault in a structure formed of the composite material is therefore required.

Figure 3C:
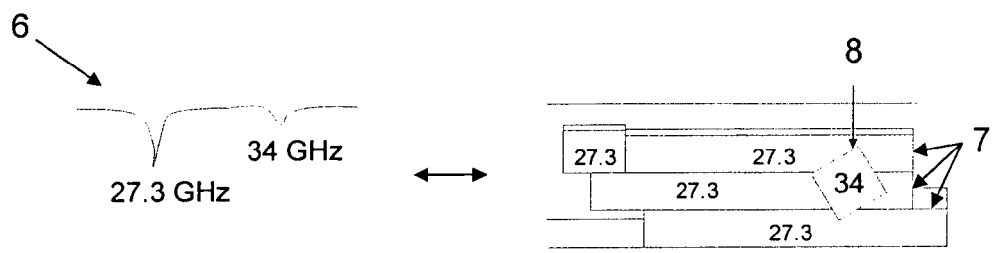

In the case of using the first mechanism, a passive resonant sensing method as illustrated in FIGS. 3a to 3c, is typically used. Referring to FIG. 3b, a system output 6 at an example frequency of 27.3 GHz corresponds to an RF signal reflected from polymer panel components 7 of a structure formed of a material having embedded sensing elements, for example nanoparticles, having electron distribution and/or transport properties that change in response to a change in a physical or chemical property of the material. In this example, a frequency of 27.3 GHz, which is the predetermined and expected dip in the frequency spectrum of the reflected signal for this composite material, is reflected from each part of each of the panel components 7 interrogated, indicating that no fault is present.

Referring to FIG. 3c, the system output 6 indicates an anomaly or fault 8 in an area of the structure components 7, as evidenced by a frequency output 6 of 34 GHz, the extent of the frequency change being indicative of the magnitude of the parameter being sensed. The precise position of this fault 8 can be determined by narrowing the width of the radiobeam, either by antenna adjustment to produce a more collimated beam, or by positioning the antenna closer to the structure, to narrow the size of the inspection area. If the component to be replaced or repaired is small, higher frequency radio signals would be used to enhance resolution of the fault region. This reveals changes in the environment as defined by the polymer enclosing each nanoparticle.

A second mechanism employs embedded particles that do not couple in a resonant manner to the particle motion, but instead lead to the generation of harmonic frequencies of the original instigating radio signal. The level of the harmonic generation, which relates to a change in connectivity between the particles in the matrix, is then monitored.

Figure 4A:
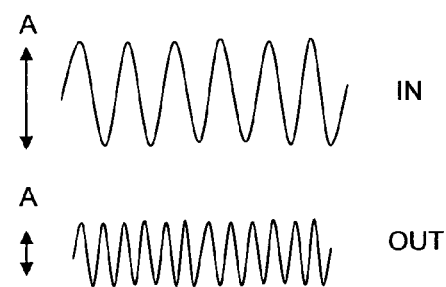
FIGS. 4a to 4c show further examples of outputs obtained when employing a system according to the invention.
Figure 4B:
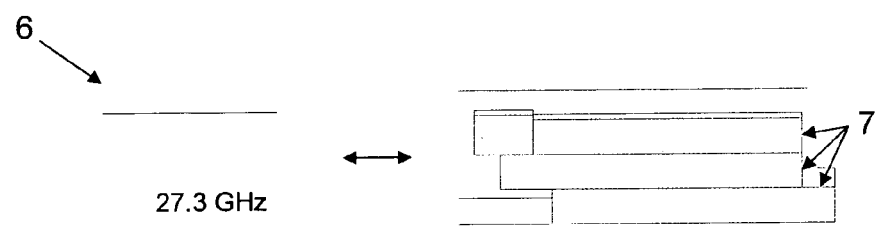
Figure 4C:
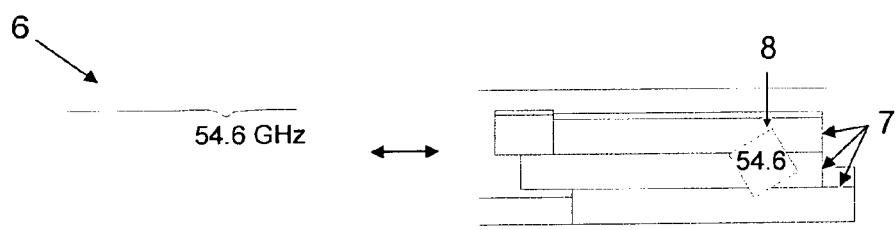

In the case of using the second mechanism, an active harmonic sensing method, as illustrated in FIGS. 4a to 4c, is typically used. This active method preferably involves monitoring the amplitude ratio between the interrogating signal going into the nanocomposite and the signal that is returned from the nanocomposite material at twice the frequency of the interrogating signal.

FIG. 4a shows examples of the interrogating RF signal (IN), having a fundamental frequency F, and the returned RF signal (OUT), having a doubled harmonic frequency 2F, whose amplitudes are indicated as A1 and A2, respectively. The amplitude ratio of A1/A2 is determined and tracked. This ratio is important as it summarises the local interactions between the particles and therefore the exact status of the polymer material.

In FIG. 4b, the output 6 does not show a response to the selected interrogation frequency of 27.3 GHz. However, as shown in FIG. 4c, a received signal of 54.6 GHz, which is double or a higher harmonic of the interrogating signal and above the ambient level, indicates the presence of a fault 8 in one of the polymer panel components 7.

In fabricating the composite matrix material 3, it is preferable that the sensing elements 4 are substantially equally spaced within the material to allow efficient and consistent sensing. However, it is possible to increase the density of the sensing elements 4 in the material 3 at points of potential weakness, such as joins or bends, if required.

In one example, a proportion of the particles of the polymer matrix are replaced by pores or "holes", typically of micrometre or nanometre dimensions, which act as sensing elements. The holes comprise a gas or fluid, typically air or water. Each pore functions as a polarisable particle. The pore count is preferably relatively low to avoid connectivity between pores. This arrangement is advantageous as it avoids the expense of purchasing specific particles, such as nanoparticles, and the process of dispersing these particles in the matrix material. The addition of pores increases the choice of materials that can be used in the sensing system.

It should also be understood that in some cases the use of different types of sensing elements 4 influence which particular parameter is sensed. The use of multiple element types is possible and offers multiple parameter measurements from a single material 3.

A further advantage of the system and method described above is that the radio signal can help in repairing any fault that is detected in the structure. For example, a microwave signal can also heat the site of damage, such as a crack in the structure, in order to repair it. A concentration of heat is provided to the damaged region because the crack is more electrically resistive, so microwave induced currents heat the crack via Ohm's law.

The intrinsic sensing system and method describes above are especially suited to hostile environments where remote sensing is desirable. The intrinsic sensing system and method give rapid access to information about structural materials, both during manufacture and within the end application, conveniently at very low cost compared to current SHM systems and methods.

The materials employed are typically construction materials where information on wear, damage or temperature is sought. The embedded particles are selected so as to provide information on change in the environment of the material, such as a change in stress, strain, temperature, pH, hydration, volume distortion, density fluctuations, contamination, radiation or icing of the material. A change in the environment of the particles can also occur due to creeping or instability within the material over time, which degrades the material's performance.

The present invention therefore allows the continuous or selective collection of data concerning critical structural components, such as structural components for the aerospace industry (such as aircraft wings, panels, bolts, vessels and seals) and smart seals for the oil and gas industry, without the need for installing any extra sensors on or in the structure; these structures are simply formed from the material described above. This also presents a far more economical SHM system, reducing aircraft maintenance and repair costs in industries which increasingly use composite materials to form such structural components. The wear or fatigue status of the component can be collected in real time, so that the time of replacement is clear, and the downtime, control and operating costs in manufacturing and in use of the component are reduced. The manufacturing process can also be closely monitored and optimised with feedback from the interior of the material.

In the field of pipeline sensing, the system and method of the invention enable continuous strain monitoring, allowing operators to prevent problems such as leaks arising. By contrast, current fibre optic techniques recognise a "hot spot" or "cold spot" that indicates the presence of a leak in liquid or gas systems, respectively, only once the leak has occurred.

The invention also improves the robustness of monitoring systems, such as downhole monitoring, removing the need for connectors and wires. The need for sensor devices to have separate power sources is also removed, as power is provided to the sensing elements via wireless interactions. Other application areas include composite quality control, aircraft and high speed brake systems, human health monitoring, pressure monitoring in nuclear and chemical plants, temperature measurement of heat shields and nose cones, and crack detection in space stations, railway lines and tankers.

What makes the present invention possible is the resonance of several materials. The present invention uses the microwave resonances that occur in many materials. There are mechanisms related to electronic and nuclear properties, which can be detected with equipment that is sensitive to radio signals. These include systems for dielelectric measurement, reflected power, IR imaging, spectral analysis, surface impedance and others. The following examples of intrinsic sensing use dielectric measurements. The first of these is a quartz chip that responds to viscosity and the second is a Multi-Wall NanoTube (MWNT) nanocomposite that responds to temperature and pressure.

Figure 5:
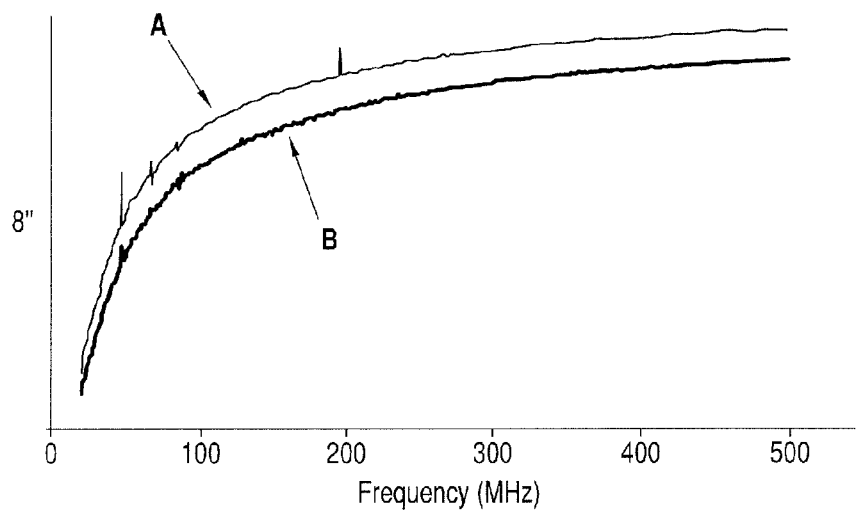
FIG. 5 shows a graph of resonances of a quartz chip in air in contact with a viscous solution.

Quartz chips are recognised acoustic resonators. Inside, phonons move easily between the faces of the chip to create acoustic standing waves. These resonances occur at multiple frequencies and can be detected as a voltage across the chips. Importantly for the purposes of the present invention, the radio properties of the chips also change, which can be determined by measuring the dielectric properties of the chips. The dielectric properties of a quartz chip are shown on curve "A" of FIG. 5. The spikes are caused by the acoustic resonances. They come superimposed on a dielectric curve typical of most insulators. Sensing is demonstrated by adding a sugar water solution which damps the resonance, as shown in curve "B"

of FIG. 5. As can be seen, peaks get wider and shorter and almost disappear as a result of the viscous damping.

Preferably, the present invention uses multiwall Carbon NanoTubes (CNTs) dispersed in a polymer. The CNTs have discernable resonances in the radio spectrum. They are monitored to detect change in the polymer due to, for example, temperature.

Figure 6:
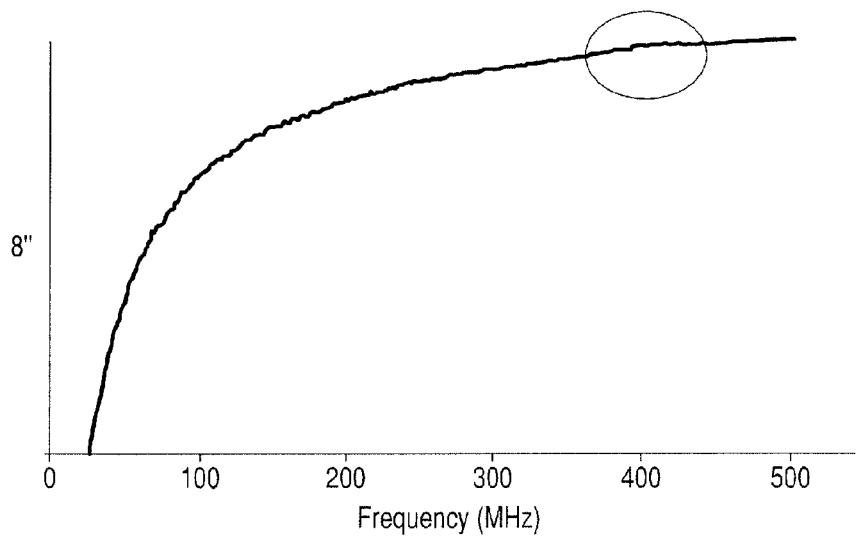
FIG. 6 shows a graph representing microwave resonances of a Carbon NanoTube (CNT) polymer composite.

As shown in the example of FIG. 6, resonances are found at 400 MHz. These are energy gaps (based on inter-wall energy difference) or phonon related resonances (based on length), and have the same frequency for best signals. In order to measure temperature change, the higher frequency peak is tracked, as a change in resonance frequency is easier to resolve. For CNT particles, a polymer resonance is wide and short, so the curve is normally fitted to a lorentzian function to find the centre frequency, which changes with temperature by approximately $10^3$-$10^4$ ppm/° C.

Figure 7:
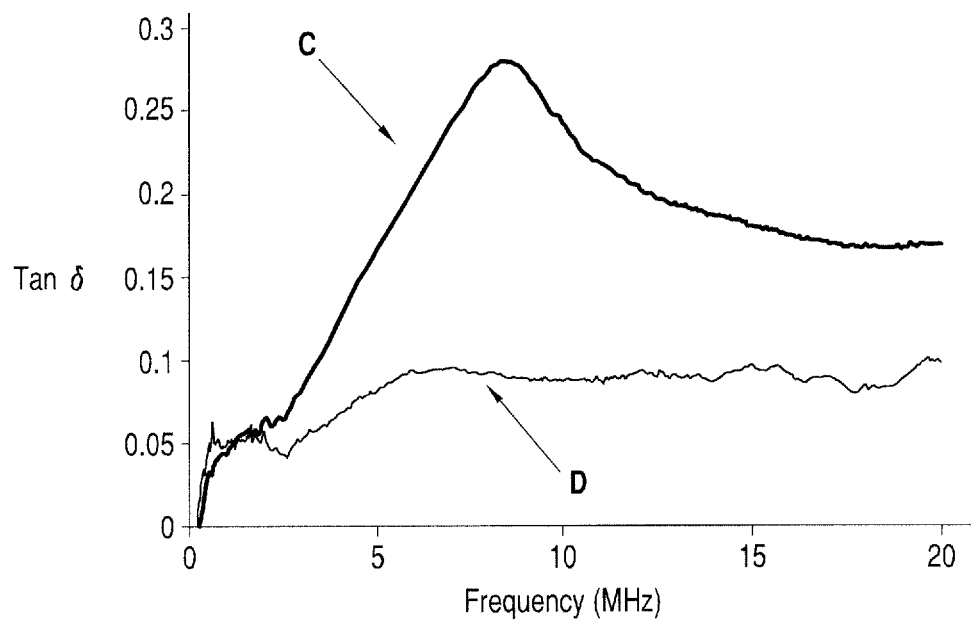
FIG. 7 shows a graph representing the microwave resonances of a multi-wall nanotube composite at 9 Ghz, versus a sample with no nanotubes.

At higher frequencies, larger radio resonances based on a percolation mechanism occur, which can give temperature or strain signals from small components, such as rivets, screws or wires or, alternatively, via far field electromagnetic signals reflected off panels and other components at distances of several metres. The magnitude of this resonance signal is demonstrated with multi-wall nanotubes buttons of various dimensions. These resonate with significant loss tangents around 9-10 GHz, or at lower frequencies when wt % is increased, as shown in FIG. 7 in which curve "C" represents the microwave resonances of a multi-wall nanotube composite at 9 Ghz and curve "D" represents a sample with no nanotubes.

Pressure reduces the resonance frequency, because CNTs move closer together, increasing conductivity across a range of frequencies. Conductivity loss dominates at low frequency so the level of the peak's left side increases, thereby appearing left shifted. On the other hand, the level of the peak's right side falls, thereby also appearing left shifted.

Figure 8:
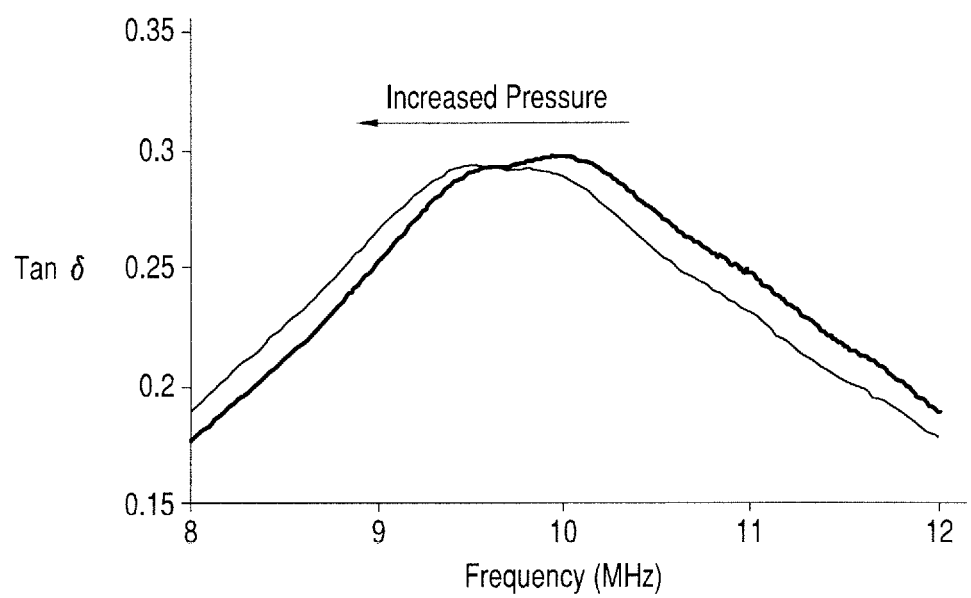
FIG. 8 shows a graph representing GHz resonances of decreasing pressure (from left to right)

The final result is that the whole peak appears to shift to the left under pressure, as shown in FIG. 8. This phenomenon will herein be referred to as the percolation threshold frequency.

The percolation threshold frequency (PTF) is a turning point that arises from two separate processes: conductivity loss and evanescent penetration, each of which have curves trending in opposite directions. In general, the dielectric loss factor increases with frequency while the evanescent depth, and therefore the size of the lossy volume, falls with frequency according to the electro-magnetic skin depth. The turning point is when both balance. This number conveniently relays changes in strain, temperature or other.

This type of resonance is not a relaxation process. Instead, there is a change of state so the radio wave either senses a dielectric at low frequency, or a reflective conductor at high frequency. The result is an intrinsic sensing material that has a radio 'colour' that can be tracked.

To make intrinsic sensors, resonant particles go into a material common to the application. This could be a polymer, gel, sol-gel, paint, adhesive or even a ceramic material. These materials come in different parts: rings, tubes, plates, screws, sheets, o-rings, grommets, washers, valves and other forms, inside buildings, boats, cars, aircraft and many others.

As examples, we consider intrinsic sensors made from o-rings, pipes and grommets to sense their environment. These sensors could also be secondary composites, where the composite material mates to another metal/ceramic part. Alternatively the sensors could be made of a novel material that improves the properties of electrical circuits or antennas, for example to add to or replace the antenna components of RFID tags, or to work with the antenna of the RFID tag to boost coupling.

The shape/size of the component part can also work with the particle resonance to enhance signals levels. This happens when the part has a natural microwave resonance that matches the particle resonance. One of the preferred objects where this effect is strongest is the o-ring structure. With the right conductivity, a nanocomposite o-ring can resonate at the particle resonance or PTF when the circumference of the o-ring is multiple electrical wavelengths.

Figure 9:
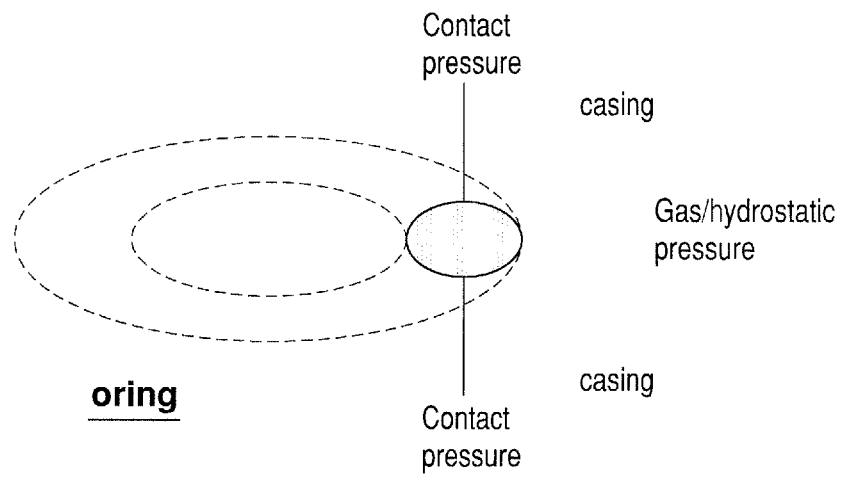
FIG. 9 shows an O-ring intrinsic sensor geometry responding to contact pressure and gas/hydrostatic pressure.

FIG. 9 shows a typical o-ring configuration where radio resonance of a o-ring is monitored via a transmission line and antenna during operation to reveal abrasion, chemical/thermal degradation, extrusion, overcompression or damage during assembly.

Figure 10:
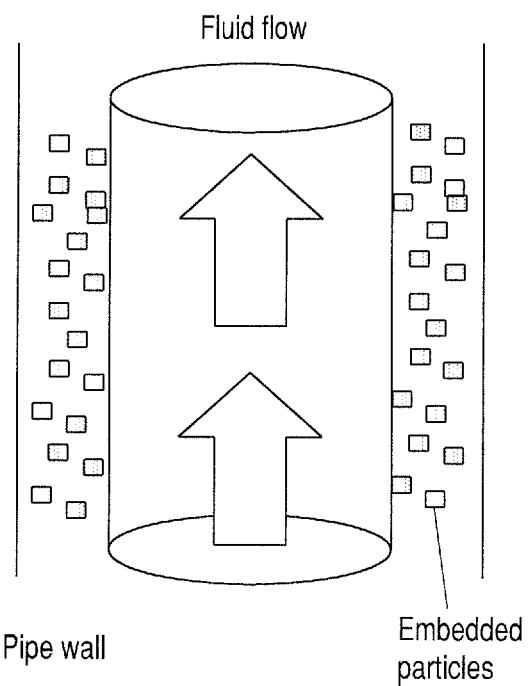
FIG. 10 shows a composite pipe intrinsic sensor geometry, where acoustically resonant particles are incorporated throughout the wall, but only those on the inside surface are in favourable conditions to oscillate and have damping related to the solution viscosity.

For reliability in harsh environments, the present invention can make use of the structure as a sensor. A good example is measurement of water viscosity inside a pipe, as shown in FIG. 10. Viscosity measurement in harsh environments leaves conventional sensors vulnerable, as they protrude into fast and turbulent fluid flow. Whereas intrinsic sensing systems are more robust by using a combination of the inside wall of a tube to collect information, and an antenna positioned outside of the harsh environment. From here, the antenna excites acoustic waves in the particles, which in turn is damped by the solution. If they are piezoelectric particles, a key aspect of the structure is that the particles are activated, possessing sharper resonances where they contact the solution, This is due to the polarising effect of the water dielectric, which increases the potential across the crystal and low acoustic damping of the inner surface particle relative to those embedded in the interior of the polymer.

Figure 11:
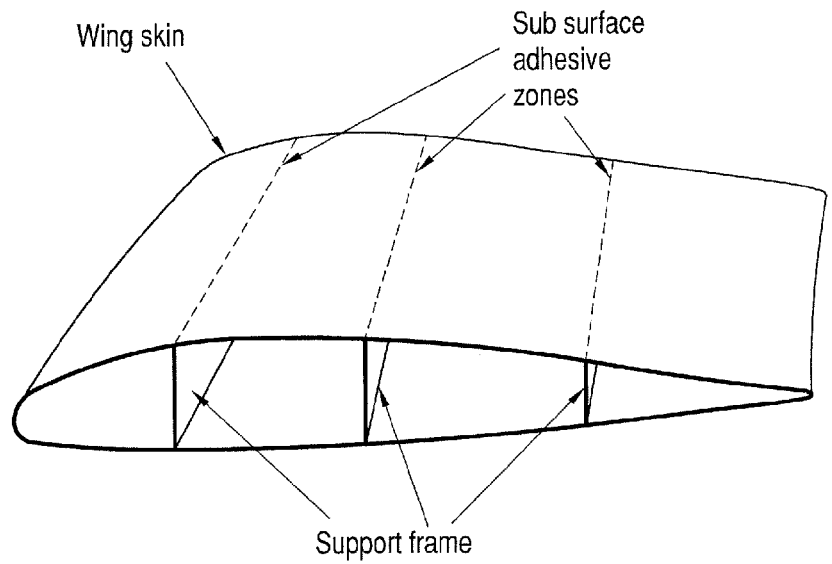
FIG. 11 shows a composite aircraft wing, incorporating intrinsic sensing adhesive at surfaces mating the skin with the support frame, providing feedback on disbonding and strain at bonding points, where structural forces are often at their highest.

FIG. 11 shows a composite aircraft wing, incorporating intrinsic sensing adhesives at surfaces mating the skin with the support frame. These areas are often hotspots of stress in panels or other load bearing structures, and convey information on their mechanical status. For this reason, key mechanical information for a composite structure is available at the bonding points.

Figure 12:
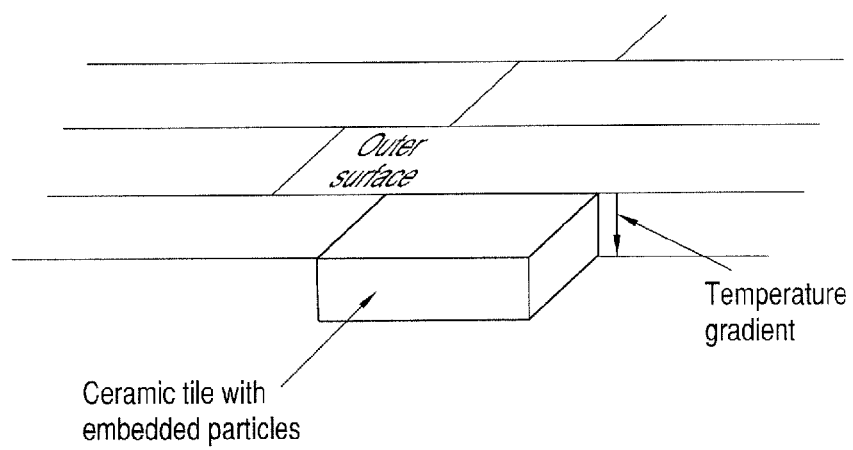
FIG. 12 shows the present invention used for the monitoring of the integrity of heat tiles.
Figure 13:
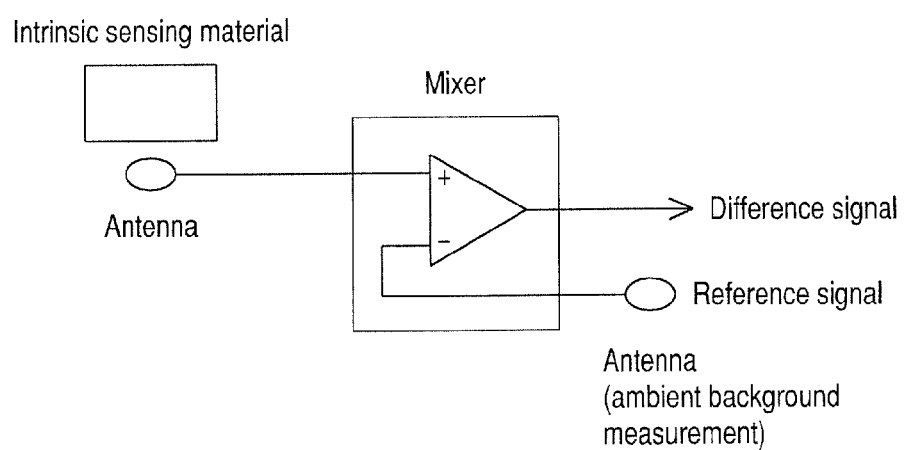
FIG. 13 shows a schematic of an intrinsic sensing system based on an ambient measurement approach.

Another area where the present invention can be used is that of monitoring the changes in the integrity of heat tiles exposed to intense heat, either for terrestrial applications or for use on the heat shield of a craft about to enter the earth's atmosphere, as shown in FIG. 12. The key aspect is to incorporate particles that are radio resonant, but only in regions where thermal conduction limits the temperature so that it is below the melting point of the particle. From this layer and further into the interior of the vessel, intrinsic sensing provides an indication of the integrity of the tile, and whether it is still in place.

Another aspect of the present invention is that of the ambient method. The ambient method intends to simplify intrinsic sensing systems by removing the transmitter so a radio license is not needed. It uses ambient radio signals to find the resonant frequency of the intrinsic sensing material. In order to do this, two antennas need to be used, one placed next to the intrinsic sensing material, and the other away from it, as shown in FIG. 12. When the two antenna signals are compared, the one from the intrinsic sensing material will lack background radio energy at the materials resonant frequency, whilst the reference antenna will not.

Accordingly, the difference between antenna signals, collected via a mixing circuit (or similar) will give the resonance frequency of the material.

The invention claimed is:

1. A sensing system comprising:
a material having a matrix structure, composed of an elastomer or epoxy resin, in which a plurality of sensing particles are embedded such that the sensing particles are dispersed within and surrounded by the matrix structure, the sensing particles include nanoparticles comprising at least one of single wall carbon nanotubes, multiwall carbon nanotubes, gold nanorings, magnetic nanoparticles, nanowires and spherical nanoparticles, and the sensing particles have electron distribution and/or transport properties that change in response to a change in a physical or chemical property of the material such that the sensing particles that exhibit a microwave resonance behaviour that leads to harmonic generation and frequency doubling; and
a receiver, including an antenna, the receiver arranged to receive, from the material, a returned RF signal resulting from interrogation of, the material by a source RF signal;
a coupling mechanism facilitating the exchange of RF energy between the material and the antenna; and
circuitry arranged to determine at least one of the mechanical, electrical and chemical status of the material;
wherein a change in the electron distribution and/or transport properties of the sensing particles cause the returned RF signal to change, such that a change in a property of the material can be determined from the returned RF signal.

2. The sensing system according to claim 1, wherein the sensing particles are arranged to alter dielectric properties of the material.

3. The sensing system according to claim 1, wherein the sensing particles are arranged to alter magnetic properties of the material.

4. The sensing system according to claim 1, wherein the sensing particles include pores.

5. The sensing system according to claim 1, wherein the resonance frequency of the sensing particles is changed by a change in an electrical and/or mechanical property of the material.

6. The sensing system according to claim 5, wherein the sensing particles comprise particles that cause the change in the returned RF signal via magnetostriction, converse piezoelectricity, magnetic direct generation or electron coupling, such that resonance is induced in the returned RF signal.

7. The sensing system according to claim 1, wherein the resonance Q factor of the sensing particles is changed by a change in an electrical and/or mechanical property of the material.

8. The sensing system according to claim 1, wherein the sensing particles are arranged, upon interaction with the source RF signal, to generate harmonic frequencies of the source RF sign al in the returned RF signal.

9. The sensing system according to claim 1, wherein the material comprises a polymer.

10. The sensing system according to claim 1, wherein the material comprises a nanocomposite material.

11. The sensing system according to claim 10, wherein the material comprises an elastomer or epoxy matrix.

12. The sensing system according to claim 1, wherein the sensing particles are substantially equally spaced within the material.

13. The sensing system according to claim 1, wherein the change in the property of the material is in response to an environmental change, the environmental change being a change in stress, strain, temperature, pH, hydration, volume distortion, density fluctuations, contamination, radiation or icing of the material.

14. The sensing system according to claim 1, wherein the source RF signal is pulse, frequency, phase or digitally modulated.

15. The sensing system according to claim 1, further comprising:
at least one transmitter, wherein the at least one transmitter is arranged to transmit the source RF signal.

16. The sensing system according to claim 8, wherein the sensing system is arranged to determine an amplitude ratio between the source RF signal generated by a transmitter and the returned RF signal at twice the frequency of the source RF, in order to monitor local interactions between the sensing particles.

17. The sensing system according to claim 15, wherein the source RF signal is arranged to heat a site of the material at which the change in the property of the material is determined.

18. The sensing system according to claim 1, wherein the antenna comprises a directional antenna.

19. The sensing system according to claim 1, wherein the antenna comprises one of a parabolic or a phase array antenna structure.

20. The sensing system according to claim 1, wherein the antenna is arranged to direct the source RF signal towards a predetermined target site of a structure comprising the material.

21. The sensing system according to claim 1, wherein the sensing system is arranged to determine a resonance frequency of the material as a function of time and the change in the returned RF signal is a change in the determined resonance frequency.

22. The sensing system according to claim 15, wherein the sensing system is arranged to combine the returned RF signals from plural source RF signals in order to obtain spatial information in respect of the material.

23. A method of sensing a change in a property of a material, the material having a matrix structure composed of an elastomer or epoxy resin, in which a plurality of sensing particles are embedded such that the sensing particles are dispersed within and surrounded by the matrix structure, the sensing particles include nanoparticles comprising at least one of single wall carbon nanotubes, multiwall carbon nanotubes, gold nanorings, magnetic nanoparticles, nanowires and spherical nanoparticles, and the sensing particles have electron distribution and/or transport properties that change in response to a change in a physical or chemical property of the material such that the sensing particles that exhibit either a microwave resonance behaviour that leads to harmonic generation and frequency doubling, the method comprising the steps of:
interrogating the material with a source RE signal;
receiving a returned RE signal from the material; and
determining at least one of the mechanical, electrical and chemical status of the material from the returned RF signal, wherein a change in the returned RF signal is caused by the change in the electron distribution and/or transport properties of the sensing particles.

24. The method of claim 23, further comprising the step of generating a source RF signal.

25. The sensing system according to claim 1, wherein the source RF signal comprises background radio energy.

26. The sensing system according to claim 25, wherein the receiver includes two antennae, a first of which is arranged to receive the returned RF signal and a second of which is arranged to receive the source RF signal.

27. The sensing system according to claim 1, wherein the change in the returned RF signal is a change between the returned signal received from a first position of the material and the returned signal received from a second position of the material.

28. The method of claim 24, wherein the step of determining the change in the property of the material comprises determining a change in resonant frequency of the material.

29. The method of claim 24, wherein the step of determining the change in the property of the material comprises determining a change in an amplitude ratio between the source RF signal generated by a transmitter and the returned RF signal at twice the frequency of the source RF signal.

* * * * *